United States Patent [19]

Gulliya et al.

[11] Patent Number: 5,312,919
[45] Date of Patent: May 17, 1994

US005312919A

[54] PHOTOOXIDATION PRODUCTS AND DERIVATIVES THEREOF OF MEROCYANINE-540, THEIR PREPARATION AND USES

[75] Inventors: Kirpal S. Gulliya, Dallas, Tex.; Burchard Franck, Munster, Fed. Rep. of Germany; J. Lester Matthews, Dallas, Tex.; Udo Schneider, Dülmen, Fed. Rep. of Germany

[73] Assignee: Baylor Research Institute, Dallas, Tex.

[21] Appl. No.: 898,961

[22] Filed: Jun. 12, 1992

[51] Int. Cl.$^5$ .................. C07D 239/02; A61K 31/505
[52] U.S. Cl. ...................................... 544/302; 544/314; 544/318; 544/320; 544/321; 544/323; 544/325; 544/326; 544/330
[58] Field of Search ............... 544/302, 314, 318, 320, 544/321, 323, 325, 326, 330; 514/269, 272, 274, 256

[56] References Cited

U.S. PATENT DOCUMENTS

| | | | |
|---|---|---|---|
| 3,360,523 | 12/1967 | Loux | 544/302 |
| 4,029,662 | 6/1977 | Vida | 544/302 |
| 4,046,894 | 9/1977 | Samour et al. | 544/302 |
| 4,054,565 | 10/1977 | Vida | 544/302 |
| 4,249,005 | 2/1981 | Samour et al. | 544/302 |
| 4,329,460 | 5/1982 | Miyashita et al. | 544/302 |

OTHER PUBLICATIONS

Franck et al, CA 117-146247s (1992).
Israel et al, CA 79-87338u (1973).
Ashcroft et al, CA 106-100363w (1986).
Kato et al, CA 83-123203q (1975).
G. W. Byers, et al., "Direct and sensitized photooxidation of cyanine dyes," *Photochemistry and Photobiology*, 23, 37-43 (1976).

*Primary Examiner*—Cecilia Tsang
*Attorney, Agent, or Firm*—Winstead Sechrest & Minick

[57] ABSTRACT

This invention relates to novel photooxidation products, and derivatives thereof, of Merocyanine 540, their preparation and their uses as anticancer and antiviral agents.

5 Claims, 1 Drawing Sheet

PHOTOOXIDATION PRODUCTS AND DERIVATIVES THEREOF OF MEROCYANINE-540, THEIR PREPARATION AND USES

BACKGROUND OF INVENTION

The present invention relates generally to photooxidation products, and derivatives thereof, of Merocyanine 540, their preparation and their therapeutic uses.

Photodynamic therapy (PDT) is an ancient concept. PDT usually involves the administration of one or more photoactive agents, or dyes, to the subject to be treated followed by exposing the specific target location or target organ of the subject to light.

The emphasis on using a photoactive compound or dye as the photoactivating or light-activating compound in photoradiation or tumors or viruses is based on two important properties of the photoactive compound or dye. Firstly, the photoactive compound or dye is preferentially accumulated and retained to a higher degree in or around the target tumor or virus than in the surrounding normal body tissues. Secondly, after being retained in or around the tumor or virus, the photoactive compound or dye is properly photoactivated causing the destruction of tumor cells or virus with which the dye has associated. The destruction of tumor cells or virus occurs when they are simultaneously exposed to the dye and light of a suitable wavelength. The generally accepted mechanism of cell kill by photoactivated dye is that when activated by appropriate light, the dye undergoes an energy transfer process with oxygen to form a reactive but extremely short-lived singlet oxygen, which subsequently oxidizes and kills the cell or inactivates virus to which the dye has attached or associated as a substrate. K. R. Weishaupt, C. J. Gomer, and T. J. Dougherty, Cancer Res. 36: 2326–29 (1976); F. Sieber, Photochem. and Photobiol. 46: 1035–42 (1987).

U.S. Pat. No. 4,649,151 teaches the preparation and purification of porphyrin-type drugs. The patent also teaches the diagnosis and destruction of cancer cells with porphyrin-type drugs. In treating humans or other mammals with the drugs, light must be irradiated on the cancer cells in such a position as to uniformly illuminate the cancer cells. When cancer cells, having the porphyrin-type drugs associated therewith, are illuminated with light, the drugs are activated and thus causing the destruction of the cancer cells by a mechanism not completely understood yet. The patent also discloses several apparatus for transmitting light to different parts of the body.

U.S. Pat. No. 4,614,190 discloses that while a dye such as hematoporphyrin derivative ("Hpd") is being held within the tumor cells in the body, the activation of the dye is accomplished by pulsed electromagnetic radiation.

U.S. Pat. No. 4,727,027 teaches the inactivation of pathogenic biological microorganisms by simultaneous treatment with furocoumarins and a long wavelength ultraviolet light under conditions which limit the availability of oxygen and other reactive species.

U.S. Pat. No. 4,684,521 teaches a chemical agent for the reduction of the population of a selected blood constituent having receptor sites. The invention uses a photoactive agent physically incorporate within or chemically bound to a carrier molecule. The carrier molecule has a strong affinity for the receptor sites on the blood constituent. When activated by Ultraviolet ("UV") radiation, the photoactive agent bound to the carrier molecule interferes with the metabolism of the selected blood constituent.

U.S. Pat. No. 4,612,322 discloses a method and system for externally treating human blood to reduce the functioning lymphocyte population in the blood system. According to the method, blood is treated with a photoactive agent and simultaneously irradiated with UV radiation outside the body.

U.S. Pat. No. 4,708,715 teaches a removable UV light array assembly for use in a patient system wherein photoactivatable agents, in contact with patient blood cells, are irradiated extracorporeally and then returned to the patient.

Cyanine dyes are members of another class of dyes that are selectively retained by tumor cells and certain viruses. For example, Merocyanine 540, (commonly referred to as MC 540) has been used for light-induced tumor and viral chemotherapy. K. S. Gulliya, J. W. Fay, R. M. Dowben, S. Berkholder and J. L. Matthews, Cancer Chemotherapy Pharmacol. 22: 211–14 (1988); K. S. Gulliya, S. Pervaiz, Blood 73: 1059–65 (1989); F. Sieber, Photochem. and Photobiol. 46:1035–42 (1987).

The currently accepted method of practicing PDT is to first let the photoactive compound bind, or get close, to the target tumor cells or viruses, and then activate the photoactive compound by a high fluence rates of light. Thus, when the reactive singlet oxygen is generated from photoactivation, the target tumor cells or viruses that are in the close proximity to the activated dye and oxygen are destroyed. The normal cells do not preferentially accumulate the photoactive compound, hence generally very little reactive singlet oxygen is generated in their close proximity. Accordingly, the normal cells are generally spared from destruction by the photoactivated photoactive compound. T. J. Dougherty, et al., Photoradiation Therapy: Clinical and Drug Advances. In *Prophyrin Photosensitization*, D. Kessel and T. J. Dougherty, Eds. Plenum Press, N.Y., pp. 3–13, 1983.

PDT, however, has one major limitation in practical utility, that is, in order to eradicate from the animal body the tumor cells or viruses on which the photoactive compound or dye neighbors or resides, such cells or viruses must be exposed to an appropriate light source. PDT is efficient only in cases where the entire tumor can be reached by light. Hence tumors thicker than 5–7 mm are rarely eradicated by PDT. Thus, to achieve the desired killing, one must find, if at all possible, the target tumor cells or viruses which have preferentially accumulated the photoactive compound, and then one must irradiate these target cells inside the animal body with a light source directly. If the tumor, such as solid tumor, is large enough and localized that it can be seen by naked eyes, then the dye can be injected into the tumor itself. Even after this, however, there is still the problem of introducing light into the inner portions of the tumor. Moreover, during metastasis, the tumor cells or viruses have spread to other parts of the body and are no longer localized. The dilemma after the introduction of photoactive compound to the patient is: Where should the irradiation be given? Even assuming that the malignant tumor cells can be localized and found in one particular body tissue or organ, many body tissues and internal organs where tumor cells or viruses have proliferated are nonetheless inaccessible to any light.

Another major limitation to PDT is that the light energy itself, in particular the ultraviolet light, is toxic and can be mutagenic to normal cells as well normal tissues. Thus, many photoactive compounds that can be activated best by ultraviolet light cannot be used in the clinic because the ultraviolet light required for the activation of the photoactive compounds would be exceedingly harmful to the surrounding normal tissues and the normal cells.

Further, patients undergoing the traditionally PDT treatment must remain in the dark for a long period of time until the photoactive agents used have cleared out of the patient's system.

To overcome many of the disadvantages of PDT, U.S. Pat. No. 5,091,385 to Gulliya, et al. discloses a pre-activated therapeutic agent derived from a photoactive compound for destroying tumor or other pathogenic biological contaminants infecting an animal body tissue. The disclosure of this U.S. patent is herein incorporate in its entirety by reference. This reference discloses that the activation of the photoactive compound is carried out prior to the photoactive compound is being brought into contact with the tissue to be treated. The resultant pre-activated therapeutic agent, or mixture or agents, retains its therapeutic activity subsequent to activation.

The method of preparing pre-activated therapeutic agent disclosed in the U.S. Pat. No. 5,091,385 often produces a mixtures of products or ingredients. Although some of the products produced by this pre-activation show biological activities, most likely, some of the products are biologically inactive.

Thus, there is a need to isolate, purify and identify the active products derived from the pre-activation of a photoactive compound. A purified active product is essential for its therapeutic uses.

SUMMARY

FIG. 1 shows MC 540 and its photooxidation products.

According to the present invention, photooxidation products, and derivatives thereof, of a photoactive compound formed under pre-activation conditions are isolated and identified. The therapeutic uses of these products are also determined.

The term "pre-activated" as used herein denotes that the photoactive compound is activated, sensitized, or excited outside the animal or human body, or outside the body tissues. Thus, the term "pre-activated" denotes that the activation of the photoactive compound is accomplished away from the body tissue to be treated, away from the target tumor cells or target biological pathogenic contaminants. Hence, the activation step in the "pre-activated" method is carried out before, not after, the photoactive compound has interacted with the target tumor cells or with other pathogenic biological contaminants. There is no requirement for further activation at the target sites once the therapeutic agent has been pre-activated. The pre-activated therapeutic agent so generated has a measurable and clinically useful shelf life-time.

The activating agent as used herein denotes a means or an agent that is capable of activating, exciting, or sensitizing a photoactive compound. The activating agent can be radiation energy, the entire spectrum of electromagnetic energy, laser, heat energy, electric current, electrons, or chemicals. The electromagnetic spectrum can be the entire range of wavelengths or frequencies of electromagnetic radiation extending from gamma rays to the longest radio waves and including visible light, xenon light, laser light, and ultraviolet light. The laser or other radiation energy can be continuous or pulsed. The pulsed energy used is such that the energy supplied has a multiple number of short pulses of relatively high energy, but at the same time, has a much lower average energy rate. The laser could be gold vapor laser, xenon laser, argon laser, a crystal laser, a gas discharge laser, an exciter laser, krypton laser, argon ion pumped dye laser, or hollow cathode metal vapor laser, and others. Even sources such as conventional filament lamp source with appropriate filtering, an arc lamp source with appropriate filtering, a fluorescent lamp, or even a pulsed xenon flash lamp with appropriate filtering could be used.

The term "interact" as used herein denotes the general phenomena of having the therapeutic agent adhering to, accumulate in the vicinity of, or associated with, the tumor cells or other pathogenic biological contaminants infecting a body tissue.

The photoactive compounds are generally compounds, such as dyes, having one or more chromophores and capable of absorbing light energy, among other forms of energy. The term "chromophore" refers to portions of a molecule that are fundamentally responsible for the electronic transition. These photoactive compounds can be cationic, anionic, zwitterionic, or neutral. They comprise chemical classes, and their respective derivatives, including, but are not limited to: acridine; anthraquinone; azine; azo, which comprises diazo, monoazo, pyrazolones, and triazo; azomethine; coumarins; diphenylmethane; flaven; flavone; flavylium salts; indigoid; methylidyne; nitro; nitroso; polymethylidyne; natural dyes such as porphyrin derivatives; psoralens; quinonimines; sulfide; sulfur; thiazole; toluidine; triphenylmethane; xanthene; and others.

The term "pathogenic biological contaminants" is to be understood to include: viruses, enveloped or not enveloped; fungi; microorganisms; parasites; bacteria and the like.

"Tumors" or "tumor cells" is understood to include, among others: cancer of the bone and connective tissues; cancer of the eyes; leukemias; lymphomas; myelomas; melanomas; breast cancer; lung cancer; ovarian cancer; brain neopleasia; as well as other types of cancer and solid tumors.

The term "body tissue" as used herein is to be understood to include "body fluid," red blood cells, white blood cells, platelets, cryo precipitate from blood plasma, other plasma proteins, bone marrow, skin, cornea, body organs, and other tissues from an animal or a human.

The term "body fluid" as used herein is to be understood to include whole blood, any formed elements of the blood, blood plasma, serum, fluids containing such components, fluids from plasmapheresis, plasma fibrinogen, cryo-poor plasma, albumin, gamma globulins, semen, and other fluids introduced or intravenously injected into the body of a patient or an animal using known administration techniques. The term "body fluid" is to be understood to include body fluid prior to, or after, physical as well as chemical fractionation, separation or freezing.

The term "external" as used herein is to denote outside the animal or human body.

The term "animal" as used herein is to denote any warm-blooded animal; this includes human and other domestic and farm animal.

The phrase "pharmaceutically acceptable carrier" as used herein includes any and all solvents, dispersion media, coatings, polymers, such as Merrifield-polystyrene, antibacterial, antiviral, antitumor, and antifungal agents, isotonic and absorption delaying agents and the like. The term "carrier" denotes a vehicle, a solution containing water, buffers, serum, serum proteins, lipoproteins, artificial bio-membranes, liposomes, monoclonal antibodies, carbohydrates, cyclodextrans, organic solvents, or other pharmaceutically acceptable, or compatible, solutions. The carrier, or vehicle, is to dissolve or carry any of the active product isolated from the above-described photoactive compound and to enhance its delivery into effective proximity to the target tumor cells or other pathogenic biological contaminants infecting body tissues. The final carrier, or vehicle, used is pharmaceutically compatible in that it is relatively non-toxic to the normal cells and normal tissues and it does not react with the solute or therapeutic agent contained therein.

The phrase "chemomodifying agent" as used herein is to denote an agent, such as a chemical or any other agent, that can potentiate, augment or increase the therapeutic efficacy of a therapeutic agent. Hence, a chemomodifying agent can synergize the therapeutic efficacy of a therapeutic agent.

The phrase "effective amount or dosage" as used herein is to denote the concentration or level of the therapeutic agent that can attain a particular medical end, such as a cure or a destruction of the undesirable cells, such as tumor cells, or pathogenic biological contaminants, without producing any pronounced toxic symptoms.

The biologically active products isolated and purified from a pre-activated compound can find therapeutic uses and be administered by standard routes, such as orally, intravenously, intramuscularly, subcutaneously, parenterally, intraperitoneally, topically or others. Solution of the biologically active products may also be mixed with a surfactant, such as hydroxypropylcellulose. Dispersion can also be prepared in glycerol, liquid polyethylene glycols, and mixtures thereof and in oils. In storage, a preservative may be utilized. These biologically active products can also be used in a blood bank setting to purify and sterilize body fluids.

The pre-activated therapeutic agents comprise a photoactive compound dissolved in a suitable medium to produce a resultant solution. The medium can be any and all solvents or mixtures thereof. To this resultant solution is introduced a sufficient amount of activating agent such that the photoactive compound is activated to produce a therapeutic mixture. The therapeutic mixture is characterized in that subsequent to activation, it is still capable of interacting with and destructing or destroying tumors or other pathogenic biological contaminants infecting body tissues, and that subsequent to activation, it is, at effective dosages, relatively non-toxic to normal tissues or normal cells. Further, its therapeutic properties are retained, in whole or in part, for at least a time period to be of practical use at ambient temperature subsequent to activation. Depending on the photoactive compound used, the stability of the resultant therapeutic agent or mixture can vary. Nevertheless, it is stable at room temperature for at least a time period to be clinically and practically useful. Some of the pre-activated therapeutic agent or mixture is even stable for days if kept in the dark and at low temperature. The term "stability" as used herein denotes the ability for the pre-activated therapeutic agent or mixture to exert its biological or therapeutic properties after storage.

The two phrases "therapeutic mixture" and "therapeutic agent" as used herein are interchangeable in that the step of activating a photoactive compound with an activating agent may yield a single product or a mixture of products, all or one or more than one product in any combination of which are biologically or therapeutically active.

Photoactive compounds which are selective for tumor or other pathogenic biological contaminants, and which can be used in the eradication or destruction of such tumor cells or contaminants in accordance with the present invention, must satisfy the following criteria:

(1) These photoactive compound must have one or more chromophores. Portions of their molecules must be fundamentally responsible for the electronic transition. They are capable of absorbing light energy;

(2) These photoactive compounds must be capable of being activated or sensitized by an activating agent, such as radiation energy, electromagnetic energy, electrical energy, electrons, ultrasound, or chemical;

(3) After they have been activated by an activating agent outside the body or body tissue, the resultant therapeutic mixture or product must still retain, in the animal body or body tissue, its preferential toxicity, toward tumors or other pathogenic biological contaminants infecting the animal body or body tissue;

(4) After they have been activated by an activating agent outside the body or body tissue, the resultant mixture or product does not require further activation by the activating agent inside the animal body or body tissue;

(5) After they have been activated by an activating agent outside the body or body tissue, the resultant therapeutic mixture or product must be relatively stable and that it must retain its biological or therapeutic activities for at least a time period at room temperature to be of practical use, such as more than a few seconds or minutes, and some for days if kept in the dark and under low temperature;

(6) After they have been activated by an activating agent outside the body or body tissue, the resultant therapeutic mixture or product is preferentially associated with tumor cells or other pathogenic biological contaminants over normal body tissues or normal cells;

(7) After they have been activated by an activating agent outside the body or body tissue, the resultant therapeutic mixture or product is efficient in destructing or destroying the tumor cells or other pathogenic biological contaminants with which it has associated;

(8) After they have been activated by an activating agent outside the body or body tissue, the resultant therapeutic mixture or product, in effective doses, is relatively non-toxic against normal cells or normal body tissues;

(9) After they have been activated by an activating agent outside the body or body tissue, the resultant therapeutic mixture or product can be combined with certain other agents to achieve a greater percentage kill of the tumor cells or other pathogenic biological contaminants infecting an animal, such as human, or a body tissue; and

(10) After they have been activated by an activating agent outside the body or body tissue, the resultant therapeutic mixture or product can be combined with certain other chemomodifying agents, such as a chemical, electrons, electrical current, or gamma rays, to augment or enhance the therapeutic effect of the resultant therapeutic mixture.

Generally, a stock solution of the pre-activated therapeutic agent or mixture is prepared by dissolving an appropriate concentration of photoactive compound in a suitable medium to give a resultant solution. The resultant solution is then subjected to a sufficient amount of activating agent to produce a therapeutic product or mixture such that the photoactive compound dissolved therein is activated and subsequently, in the absence of the activating agent, capable of interacting with, and destroying, tumors or other pathogenic biological contaminants infecting the body tissues. Aliquots of the stock solution are then removed and diluted with appropriate pharmaceutically acceptable carrier or vehicle to the desired concentrations.

Some of the preferred activating agent include, but are not limited to: radiation in the entire absorption spectrum or region of the photoactive compound, preferably around the relatively strong or near maximum absorption regions of the molecules; gamma rays; electrons generated by an electropotential device; and chemical.

Any suitable source can be employed to irradiate the photoactive compound, provided such source produces sufficient radiation to activate the photoactive compound and to provide the resultant therapeutic agent or mixture with the desired properties mentioned above. The operable source employed to irradiate the resulting fluid has a wavelength of from about 230 nm to about 1200 nm and an energy density of from about 0.1 J/cm$^2$ to about 3000 J/cm$^2$. Suitable light sources include, but are not limited to, sources that generate a specific wavelength range of radiation and sources that are fitted with appropriate filter to reduce the undesirable ranges of wavelengths.

Because the pre-activation of the therapeutic agent, or the activation of the photoactive compound, takes place before, not after nor during, the agent or compound is brought into contact with tissues, i.e. extracorporeally or outside the body, the activating agent used can even be a potentially lethal or dangerous radiation, such as UV or gamma rays. The UV or gamma rays used to activate the photoactive compound will not be in contact with any body tissue. Hence, they will not harm the body tissues or the host, such as the human subject or patient.

Flow of electrons or electric current, such as that generated by two electrodes, can also be used to activate the photoactive compound. The electrodes are made of a cathode and an anode. They can be powered by any conventional power source, such as a direct current battery or others. The operable voltage or current has a low amperage but high voltage, such as from about 100 volts to about 5000 volts in a range of milliamps. Certain chemicals, such as chloroquine, hydrogen peroxide, certain reducing agents or certain oxidizing agents can also be used to activate the photoactive compound.

DESCRIPTION OF PREFERRED EMBODIMENTS

Figure 1:
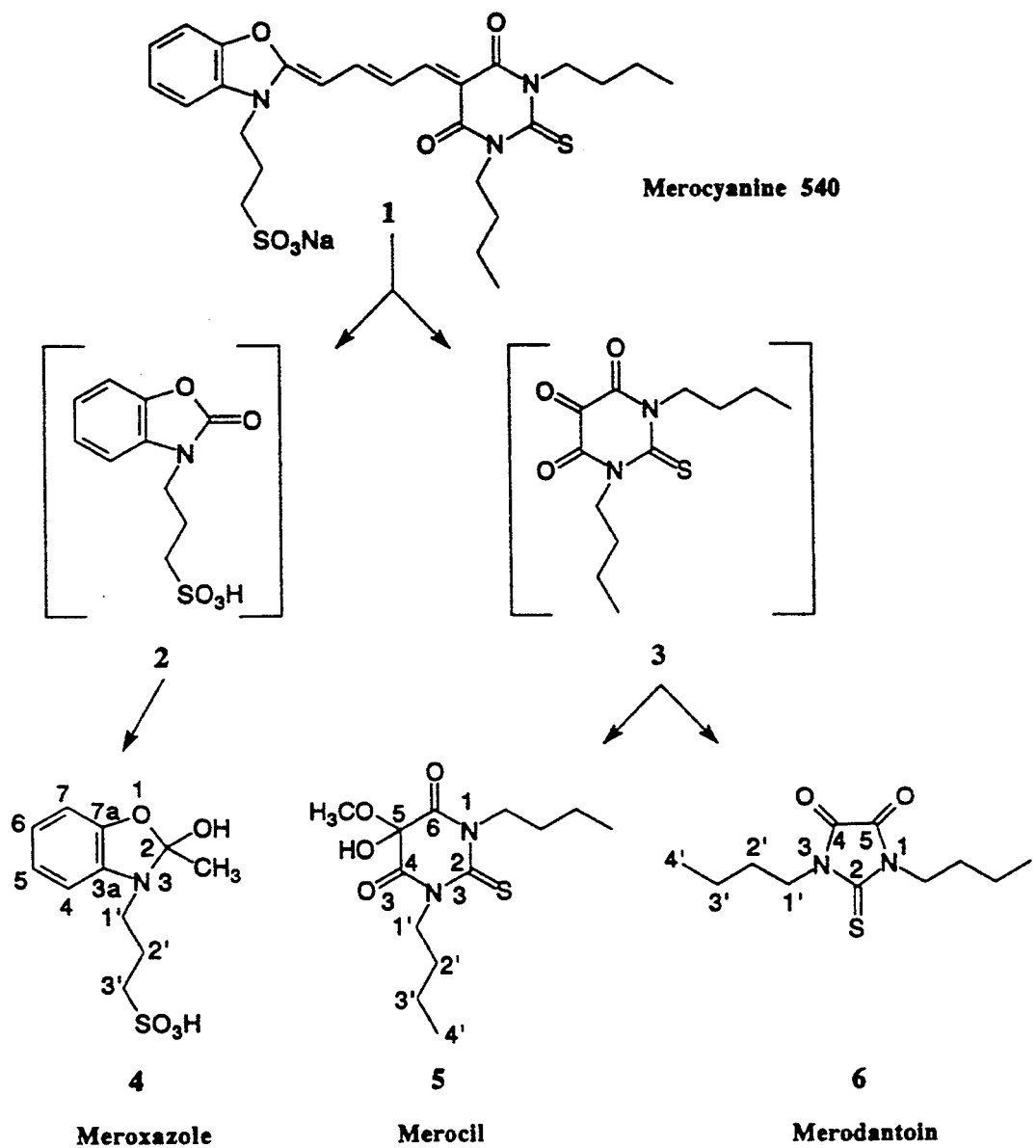

Broadly, the method for identifying active products from a photoactive compound, which is capable of being pre-activated, comprises the steps of: Firstly, activating an appropriate concentration of the photoactive compound in a suitable medium with a sufficient amount of an activating agent to give a mixture of products; secondly, separating said mixture of products by a suitable means, such as chromatography, to give a number of relatively pure products; thirdly, evaluating the biological activity of each of the relatively pure product by an acceptable biological method, such as a standard in vitro or in vivo testing method; and lastly, selecting the relatively pure product that shows biological activity by the evaluating step.

The present invention relates generally to photooxidation products, and derivatives thereof, of Merocyanine 540, their preparation and their therapeutic uses.

Some of the photooxidation products and their derivatives are:

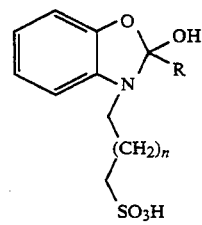

which comprises racemic mixture of optically active compounds, wherein: n=0, 1, or 2; and R=H, $C_1$-$C_6$ linear or branched alkyl, or $CH_2C_6H_5$; or pharmaceutically acceptable salts thereof.

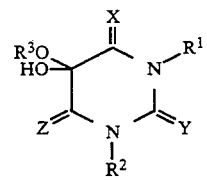

which comprises racemic mixture of optically active compound, wherein: $R^1$=H, $C_1$-$C_6$ linear or branched alkyl, or $CH_2C_6H_5$; $R^2$=H, $C_1$-$C_6$ linear or branched alkyl, or $CH_2C_6H_5$; $R^3$=H, $C_1$-$C_6$ linear or branched alkyl, or $CH_2C_6H_5$; X=O, S, or NH; Y=O, S, or NH; and Z=O, S, or NH; or pharmaceutically acceptable salts thereof.

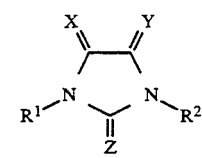

wherein: $R^1$=H, $C_1$-$C_6$ linear or branched alkyl, or $CH_2C_6H_5$; $R^2$=H, $C_1$-$C_6$ linear or branched alkyl, or $CH_2C_6H_5$; X=O, S, or NH; Y=O, S, or NH; and Z=O, S, or NH; or pharmaceutically acceptable salts thereof.

EXAMPLES

Material. Merocyanine 540, compound 1, (MC 540; 1,3 dibutyl- 5-[4-[3-(3-sulfopropyl)-2-benzoxazolinylidine]-2,4-butenylidene]-2-thiobarbituric acid sodium salt) was purchased from Eastman Kodak in Rochester, N.Y. and used as received.

Spectrometers. UV/VIS spectra: Shimadzu UV 160; FT-IR spectra: Biorad Digilab Division FTS 45, measurements in $CH_2Cl_2$ and in KBr; Mass spectra: Finnigan MAT 312, EI measurements at 70 eV; $^1H$ NMR spectra: Bruker WM 300 and WM 360, TMS as internal standard; $^{13}C$ NMR spectra: Bruker WM 360, with proton broad band decoupling.

Photooxidation. 50 ml 0.1 % solutions of MC 540, compound 1, in methanol were irradiated in a quartz apparatus with a mercury high pressure lamp (Heraeus TQ 150 Z2, max. intensity at 530 nm) at $-25°$ C. under passing of oxygen for 30 minutes. During the irradiation the fluorescence of the solution changed from deep red to orange-brown.

Chromatographic separations. After evaporation of the solvent the photooxidation product mixture was analyzed by TLC on aluminum sheets, coated with fluorescent silica gel 60 $F_{245}$ (E. Merck, Darmstadt, Germany) and detection of the substances with iodine vapor. Solvent systems: (a) $CH_2Cl_2$/ethyl acetate (10:1); and (b) ethanol/cyclohexane (4:1). TLC with solvent system (a) showed two products of $R_f$ 0.83 and 0.65, and with system (b) six spots with the most intensive one at $R_f$ at 0.88. Column chromatography with system (a) on silica gel (E. Merck, particle size 0.063-0.200 mm) yielded merodantoin, compound 6, and merocil, compound 5. By subsequent elution with methanol, evaporation and chromatographic separation with system (b) a further photooxidation product meroxazole, compound 4, was obtained.

Meroxazole (2-Hydroxy-2-methyl-3-[3'-sulfopropyl]-benzoxazolin), compound 4: Pale yellow microcrystalline solid, 20.1% yield. $-R_f$ (system (b)):s 0.88.$-$UV/VIS (MeOH): $\lambda$max(1 g $\epsilon$)=205 nm (3.97), 272 (3.01).-FT-IR (KBr): $\nu$=3610-3180 cm$^{-1}$ (OH), 2880-2970 (OH of $SO_3H$), 1640 (arom. C=C), 1390 (S=O), 1210 (C—O—C).—$^1H$ NMR ($CD_3OD$): $\delta$=1.28 (s, 3H, $CH_3$ at C-2), 2.28 (quint, J=6.4 Hz, 2H, 2'-$CH_2$, 2,92 (t, J=6.7 Hz, 2H, 3'-$CH_2$), 4.05 (t, J=7.6 Hz, 2H, 1'-$CH_2$), 6.8-7.3 (m, 4H, arom. H, C-4-C-7).—$^-C$ NMR ($CD_3OD$): $\delta$=14.13 ($CH_3$ at C-2), 24.63 (C-2'), 31.47 (C-3'), 42.04 (C-1'), 64.25 (C-2), 110.26 (C-5), 110.75 (C-6), 123.77 (C-4), 125.31 (C-7), 133.47 (C-3a), 143.96 (C-7a).- MS: m/z (%)=273 (22) [M+], 258 (8) [M+-$CH_3$], 230 (12) [M+-$C_2H_3O$], 150 (44) [M+-$C^3H_5SO_3H$—H]. $C_{11}H_{15}NO_5S$ Calcd. 273.3032 Found 273.3034 (MS).

Merocil (N,N'-Dibutyl-4,5 dihydro-5-hydroxy-5-methoxy-4-oxo-2-thiouracil), compound 5: Pale yellow oil, 15.8% yield - $R_f$ (system (a)): 0.63. - UV/VIS ($CH_2Cl_2$): $\lambda$max (1 g $\epsilon$)=255 nm (4.170), 277 (4.179). - FT-IR ($CH_2Cl_2$): $\nu$=3480-3230 cm$^{-1}$ (OH), 2870-2940 (aliphat. CH), 1775 (C=O), 1415 (C=S), 1210 (C—O—C).- $^1H$ NMR ($CDCl_3$): $\delta$=0.94 (t, J=7.2 Hz, 6H, 4'-$CH_3$), 1.36 (sext, J=7.8 Hz, 4H, 3'-$CH_2$), 3.63 (m, 4H, 1'-$CH_2$), 3.88 (s, 3H, $OCH_3$), 4.67 (s, 1H, OH).- $^{13}C$ NMR ($CDCl_3$: $\delta$=13.65 (C-4'), 19.80 (C-3'), 29.68 (C-2'), 41.98 (C-1'), 54.83 ($OCH_3$), 84.533 (C-5), 167.72 (C-4,6), 183.17 (C-2).- MS: m/z (%)=302 (34) [M+, 269(6) [M+-HS], 243 (100)[M+-$C_2H_4O_2$], 57 (36) [$C_4H_9$+].

$CH_{22}N_2O_4S$ Calcd. 302.1300 Found 302.1302 (MS).

Merodantoin (N,N'-Dibutyl-2-thio-4,5-imidazolindion), compound 6: Orange colored Oil, 16.4% yield. $-R_f$(system (a)): 0.83. - UV/VIS ($CH_2Cl_2$): $\lambda$max (1 g $\epsilon$)=229 nm (3.71), 3.05 (3.90).- FT-IR ($CH_2Cl_2$): $\nu$=2875-2960 cm$^{-1}$ (aliphat. CH), 1770 (C=O), 1410 (C=S). - $^1H$ NMR ($CDCl_3$): $\delta$=0.95 (t, J=7.3 Hz, 6H, 4'-$CH_3$), 1.34 (sext, J=7.7 Hz, 4H, 3'-$CH_2$), 1.67 (quint, J=7.2 Hz, 4H, 2-$CH_2$) 3.93 (t, J=7.5 Hz, 4H, 1'-$CH_2$). - $^{13}C$ NMR ($CDCl_3$): $\delta$=13.54 (C-4'), 19.90 (C-3'), 29.72 (C-2'), 41,83 (C-1'), 155.35 (C-4,5), 180.62 (C-2). -MS: m/z (%)=242 (100) [M+], 209 (26) [M+- HS], 187 (22) [$C_9H_{19}N_2S$+], 86 (26) [$C_5H_{12}N$+], 57 (46) [$C_4H_9^{30}$].

$C_{11}H_{18}N_2O_2S$ Calcd. 242.1089 Found 242.1089 (MS).

The structures of the three photooxidation products of MC 540, compound 1 (FIG. 1) were elucidated by their analytical data and chemical measurements as discussed above.

Synthesis of Merodantoin, Compound 6

A solution of 3,75 ml (0,040 mol) oxalyl chloride in 15 ml of dry $CH_2Cl_2$was added dropwise at $-78°$ C. with stirring to a solution of 6,58 g (0,035 mol) N,N'-di-n-butylurea in 150 ml of dry $CH_2Cl_2$. The mixture was kept for 1 h at $-78°$ C. and afterwards allowed to warm up to ambient temperature. It was washed with water, dried over $Na_2SO_4$ and evaporated to yield a red-brown colored oil, which was washed through a silica gel column with $CH_2Cl_2$/ethyl acetate=5:1. The eluate was further purified through a second silica gel column with $CH_2Cl_2$/n-hexane=3.1 yield 770 mg of a yellow-red oil, which was identical with Merodantoin obtained by photooxidation of MC 540, according to FT-IR, NMR and MS data.

| $C_{11}H_{18}N_2O_2S$ (242,1) | | | |
|---|---|---|---|
| | H | C | N |
| calculated | 54,54% | 7,44% | 11,57% |
| found: | 54,56% | 7,61% | 11,95% |

Biological Activities of the Products

The biological activities of the photooxidation products of MC 540 were determined. The results of the assays are given in the Tables below. Preactivated MC 540 is abbreviated as pMC 540. Assays of antitumor activities of the products were carried out according to published standard methods. K. S. Gulliya, S. Pervaiz, R. M. Dauben and J. L. Matthews, Photochem. and Photobiol. 52: 831–38 (1990); and T. Mosmann, J. Immulog. Methods 65: 55–63 (1983). Assays for the antiviral properties of these products were performed according to a published standard method. G. A. Robertson, B. M. Kostek, W. A. Schleif, J. A. Lewis, and E. A. Emini, J. Virological Methods 20: 195–202 (1988). The disclosures of these references are herein incorporated by reference.

TABLE 1

A Comparison of the Cytotoxic Effects of Merocil, Merodantoin and Preactivated Merocyanine 540 (pMC 540) on Normal Human Peripheral Blood Mononuclear Cells

| Merocil | | Merodantoin | | pMC 540 | |
|---|---|---|---|---|---|
| Dose ($\mu$g/ml) | % cell kill (mean ± S.E.M.) | Dose ($\mu$g/ml) | % cell kill (mean ± S.E.M.) | Dose ($\mu$g/ml) | % cell kill (mean ± S.E.M.) |
| 0.00 | 1.33 ± 0.19 | 0.00 | 1.33 ± 0.19 | 0 | 1.33 ± 0.19 |
| 0.78 | 2.67 ± 0.80 | 1.56 | 4.33 ± 1.07 | 40 | 6.77 ± 0.85 |
| 1.56 | 5.00 ± 0.67 | 3.13 | 3.67 ± 0.51 | 80 | 8.30 ± 1.07 |
| 3.13 | 4.00 ± 0.67 | 6.25 | 5.33 ± 0.84 | 120 | 15.0 ± 1.93 |
| 6.25 | 6.0 ± 0.00 | 12.5 | 11.33 ± 1.83 | | |
| 12.5 | 5.0 ± 0.71 | 25.0 | 25.67 ± 0.51 | | |

Merocil and Merodantoin were dissolved in cremophor EL whereas pMC 540 was prepared in 10% aqueous ethanol. The solvent controls did not show measurable cytotoxic effects. Fresh human peripheral mononucleas cells (1×10⁶ cells/ml) were treated with indicated concentration of compounds. After overnight incubation at 37° C., cell viability was determined by trypan blue dye exclusion method. Mean values of three separate experiments are shown. As can be seen above, all Merocil, Merodantoin and PMC 540 are relatively non-toxic to normal human peripheral blood mononuclear cells.

As will be shown later, Merocil and Merodantoin at 12.5 and 25 $\mu$g/ml respectively cause a virtually complete growth inhibition of cultured Daudi lymphoma cells whereas preactivated Merocyanine 540 causes 88% growth inhibition at 120 $\mu$g/ml.

TABLE 2

Cytotoxic Effects of Merodantoin on Human Burkitt Lymphoma Daudi Cells

| Dose ($\mu$g/ml) | % Cell Kill (means ± S.D.) |
|---|---|
| 1.56 | 2.75 ± 3.20 |
| 3.13 | 6.25 ± 2.99 |
| 6.25 | 9.75 ± 1.71 |
| 12.50 | 42.00 ± 8.68 |
| 25.00 | 100.00 ± 0.00 |

Human Burkitt Lymphoma Daudi cells (1×10⁶ cells/ml) were treated with different concentrations of Merodantoin. After overnight incubation at 37° C., the tumor cells kill was determined by MTT assay. Results of three separate experiments are shown. The toxicity of vehicle only (dimethyl sulphoxide DMSO) control was unmeasurable at the highest concentration (5 $\mu$l/ml) tested.

TABLE 3

Cytotoxic Effects of Merocil on Human Burkitt Lymphoma Daudi Cells

| Dose ($\mu$g/ml) | % Cell Kill (means ± S.D.) |
|---|---|
| 0.78 | 4.75 ± 3.20 |
| 1.56 | 16.50 ± 9.45 |
| 3.13 | 36.75 ± 16.15 |
| 6.25 | 87.25 ± 9.90 |
| 12.50 | 100.00 ± 0.00 |

Human Burkitt Lymphoma Daudi cells (1×10⁶ cells/ml) were treated with different concentrations of Merocil. After overnight incubation at 37° C., the tumor cells kill was determined by MTT assay. Results of three separate experiments are shown as a percentage of untreated controls. The toxicity of vehicle only (DMSO) control was unmeasurable at the highest concentration (5 $\mu$l/ml) tested.

TABLE 4

Effect of Merocil and Merodantoin on Cells from Cultured Tumor Cell Lines

| Cell Type | Merocil ($\mu$g/ml) | % inhibition of cell proliferation | | Merodantoin ($\mu$g/ml) | % inhibition of cell proliferation | |
|---|---|---|---|---|---|---|
| | | 20 hr. | 5 days | | 20 hr. | 5 days |
| C-33A (carcinoma cervix, human) | 0.78 | 2 | 23 | 1.56 | 16 | 11 |
| | 1.56 | 9 | 26 | 3.13 | 29 | 34 |
| | 3.13 | 35 | 46 | 6.25 | 36 | 86 |
| | 6.25 | 36 | 89 | 12.5 | 49 | 63 |
| | 12.5 | 49 | 97 | 25.0 | 56 | 91 |
| DU 145 (prostate, carcinoma, human) | 0.78 | 0 | 26 | 1.56 | 0 | 54 |
| | 1.56 | 0 | 33 | 3.13 | 1 | 85 |
| | 3.13 | 0 | 71 | 6.25 | 8 | 99 |
| | 6.25 | 5 | — | 12.5 | 9 | 100 |
| | 12.5 | 3 | 93 | 25.0 | 11 | 100 |
| MS 751 (cervix, carcinoma, human) | 0.78 | 1 | 10 | 1.56 | 8 | 11 |
| | 1.56 | 7 | 11 | 3.13 | 24 | 23 |
| | 3.13 | 12 | 12 | 6.25 | 20 | 66 |
| | 6.25 | 20 | 29 | 12.5 | 28 | 90 |
| | 12.5 | 20 | 89 | 25.0 | 41 | 100 |
| JEG-3 (chorio-carcinoma, human) | 0.78 | 0 | 8 | 1.56 | 15 | 18 |
| | 1.56 | 3 | 11 | 3.13 | 53 | 38 |
| | 3.13 | 32 | 11 | 6.25 | 88 | 91 |
| | 6.25 | 68 | 51 | 12.5 | 100 | 100 |
| | 12.5 | 86 | 86 | 25.0 | 100 | 100 |

Each cell type (1×10⁶ cells/ml; in triplicate) was treated with indicated concentrations of merocil or merodantoin. After overnight (20 hr.) or 5 day incubation periods, the cell viability was determined by MTT assay and calculated as a percentage of untreated controls. The toxicity in vehicle only (cremophor EL) controls was not detectable at highest dose tested.

Results of a representative experiment (repeated twice) are shown.

TABLE 5

| Cell Type | Merocil (μg/ml) | % inhibition of cell proliferation 48 hr. | 4 days | Merodantoin (μg/ml) | % inhibition of cell proliferation 48 hr. | 4 days |
|---|---|---|---|---|---|---|
| BT-20 (breast, adenocarcinoma) | 0.78 | 3 | 11 | 1.56 | 0 | 19 |
| | 1.56 | 0 | 22 | 3.13 | 0 | 52 |
| | 3.13 | 2 | 41 | 6.25 | 0 | 20 |
| | 6.25 | 0 | 20 | 12.5 | 8 | 12 |
| | 12.5 | 11 | 8 | 25.0 | 26 | 73 |

Each cell type ($1 \times 10^6$ cells/ml; in triplicate) was treated with indicated concentrations of merocil or merodantoin. After overnight (20 hr.) or 5 day incubation periods, the cell viability was determined by MTT assay and calculated as a percentage of untreated controls. The cytotoxicity in vehicle only (cremophor EL) controls was undetectable.

TABLE 6

| Cell Type | Merocil (μg/ml) | % inhibition of cell proliferation 24 hr. | Merodantoin (μg/ml) | % inhibition of cell proliferation 24 hr. |
|---|---|---|---|---|
| H.S. Sultan (multiple myeloma) | 0.78 | 23 | 1.56 | 18 |
| | 1.56 | 28 | 3.13 | 34 |
| | 3.13 | 24 | 6.25 | 54 |
| | 6.25 | 63 | 12.5 | 77 |
| | 12.5 | 68 | 25.0 | 87 |
| 8226 (multiple myeloma) | 0.78 | 17 | 1.56 | 20 |
| | 1.56 | 24 | 3.13 | 16 |
| | 3.13 | 26 | 6.25 | 20 |
| | 6.25 | 25 | 12.5 | 30 |
| | 12.5 | 55 | 25.0 | 46 |
| U266B1 (myeloma) | 0.78 | 3 | 1.56 | 8 |
| | 1.56 | 6 | 3.13 | 10 |
| | 3.13 | 21 | 6.25 | 10 |
| | 6.25 | 8 | 12.5 | 12 |
| | 12.5 | 8 | 25.0 | 12 |

Each cell type ($1 \times 10^6$ cells/ml; in triplicate) was treated with indicated concentrations of merocil or merodantoin. After overnight (20 hr.) or 5 day incubation periods, the cell viability was determined by MTT assay and calculated as a percentage of untreated controls. The cytotoxicity in vehicle only (cremophor EL) controls was not detectable at highest dose tested.

TABLE 7

Effect of Meroxazole on Human Burkitt Lymphoma Lymphoma Daudi Cells

| Dose (μg/ml) | % Cell Kill |
|---|---|
| 25 | 0 |
| 50 | 0 |
| 75 | 0 |
| 100 | 0 |
| 125 | 0 |
| 500 | 32 |

Each cell type ($1 \times 10^6$ cells/ml; in triplicate) was treated with indicated concentrations of Merocil or Meroxazole. After overnight (20 hr.) or 5 day incubation periods, the cell viability was determined by MTT assay and calculated as a percentage of untreated controls. There was no observable toxicity in vehicle only (ethanol) controls up to 10 μl/ml tested in this assay.
Conclusion: Meroxazole is not cytotoxic to Daudi cells.

TABLE 8

Effect of Merocil and Merodantoin on the Inactivation of Cell Free Human Immunodeficiency Virus

| Experimental MT-4 Conditions | Drug Concentration | % viability of Target Cells |
|---|---|---|
| MT-4 cells | zero | 100.00 |
| MT-4 cells + untreated HIV-1 | zero | 36.75 |
| MT-4 cells + HIV treated with | 25 μg/ml* | 54.33 |
| | 50 μg/ml* | 43.32 |
| | 75 μg/ml* | 101.34 |
| | 25 μg/ml** | 73.50 |
| | 50 μg/ml** | 94.32 |
| | 75 μg/ml** | 101.94 |

*Merocil
**Merodantoin

Cell free human immunodeficiency virus (HIV-1) was either left untreated or treated with indicated doses of Merocil or Merodantoin for one hour at 37° C. and added to MT-4 target cells. After 4 hour incubation at 37° C., the cells were washed three times and further incubated in drug free fresh growth medium (complete RPMI-1640) at 37° C. for 4 days. On day four, 50% of the culture supernatant was replaced with fresh growth medium to prevent cell death due to possible nutrient depletion. The viability of the cell was determined on day 11 by MTT assay. Results show that the treatment of cell free HIV with a 75 μg/ml dose of either compound caused a virtually complete inactivation of the virus. The viability of the MT-4 cells was not affected by Merocil or Merodantoin under the experimental conditions described above.

TABLE 9

Combined Effect of Meroxazole, Merocil and Merodantoin on L1210 Mouse Leukemia Cells

| Treatment Compound | % Cell Kill |
|---|---|
| Control | Zero |
| MC | 28 |
| MD | 64 |
| MZ | Zero |
| MC + MZ | 22 |
| MD + MZ | 58 |
| MC + MD | 94 |
| MC + MD + MZ | 100 |

Mouse leukemia L1210 cells ($1 \times 10^6$ cells/ml) were treated with different combinations of the indicated compounds (isolated from preactivated merocyanine 540). After overnight incubation the cell kill was determined by MTT assay. Doses used were MC = 12.5 μg/ml; MD = 25 μg/ml; MZ = 25 μg/ml.
MC = Merocil; MD = Merodantoin; MZ = Meroxazole Conclusion: Each of Merocil and Merodantoin is effective in inhibiting the proliferation of certain tumor cells and in inactivating human immunodeficiency virus (HIV-1). Mixtures containing different permutations of Merocil, Merodantoin and Meroxazole also show biological activities.

While the present invention has been particularly described in terms of specific embodiments thereof, it will be understood in view of the present disclosure that numerous variations upon the invention are now enabled to those skilled in the art, which variations yet reside within the scope of the present invention. Accordingly, the invention is to be broadly construed, and limited only by the scope and spirit of the claims now appended hereto.

We claim:

1. A compound having the formula

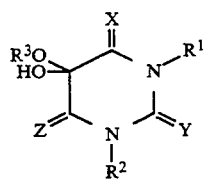

or optical isomers or mixtures thereof wherein:
$R^1$ = H, $C_1$–$C_6$ linear or branched alkyl, or $CH_2C_6H_5$;
$R^2$ = H, $C_1$–$C_6$ linear or branched alkyl, or $CH_2C_6H_5$;
$R^3$ = H, $C_1$–$C_6$ linear or branched alkyl, or $CH_2C_6H_5$;
X = O, S, or NH;
Y = S; and
Z = O, S, or NH; or
a pharmaceutically acceptable salt thereof.

2. A pharmaceutical composition comprising an amount of a compound according to claim 1 effective as an anti-carcinoma agent and a pharmaceutically acceptable carrier.

3. The pharmaceutical composition of claim 2 wherein said pharmaceutically acceptable carrier is selected from the group consisting of cremophor, dimethyl sulphoxide and mixtures thereof.

4. A pharmaceutical composition comprising an amount of a compound according to claim 1 sufficient to inhibit the replication of an HIV virus and a pharmaceutically acceptable carrier.

5. A compound having the formula

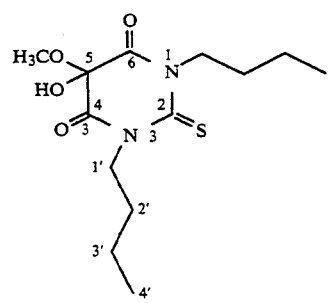

or optical isomers or mixtures thereof or a pharmaceutically acceptable salt thereof.

* * * * *

UNITED STATES PATENT AND TRADEMARK OFFICE
CERTIFICATE OF CORRECTION

PATENT NO. : 5,312,919
DATED : May 17, 1994
INVENTOR(S) : Kirpal S. Gulliya, et al.

It is certified that error appears in the above-indentified patent and that said Letters Patent is hereby corrected as shown below:

Col. 9, line 52, delete "-C NMR" and insert --$^{13}$C NMR--.

Col. 10, line 7, delete "CH$_{22}$N$_2$O$_4$S" and insert --C$_{13}$H$_{22}$N$_2$O$_4$--.

Col. 11, TABLE I, delete "Merodantoih" and insert --Merodantoin--.

Col. 13, line 47, delete "cytotoxicity" and insert --toxicity--.

Signed and Sealed this

Twenty-first Day of February, 1995

Attest:

BRUCE LEHMAN

Attesting Officer

Commissioner of Patents and Trademarks